(12) United States Patent
Dolitzky et al.

(10) Patent No.: US 7,425,627 B2
(45) Date of Patent: Sep. 16, 2008

(54) METHODS OF SYNTHESIZING OLANZAPINE

(75) Inventors: Ben-Zion Dolitzky, Petach-Tiqva (IL); Dov Diller, Jerusalem (IL)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 423 days.

(21) Appl. No.: 11/020,869

(22) Filed: Dec. 22, 2004

(65) Prior Publication Data
US 2005/0159408 A1 Jul. 21, 2005

Related U.S. Application Data

(60) Provisional application No. 60/532,126, filed on Dec. 22, 2003, provisional application No. 60/547,901, filed on Feb. 25, 2004, provisional application No. 60/561,871, filed on Apr. 12, 2004.

(51) Int. Cl.
*C07D 243/10* (2006.01)
*C07D 333/38* (2006.01)

(52) U.S. Cl. ...................................... 540/557
(58) Field of Classification Search ............. 540/557
See application file for complete search history.

(56) References Cited

U.S. PATENT DOCUMENTS

| 5,229,382 A | 7/1993 | Chakrabarti et al. | 514/220 |
| 5,637,584 A | 6/1997 | Larsen | 514/220 |
| 5,703,232 A | 12/1997 | Bunnell et al. | 540/557 |
| 5,736,541 A | 4/1998 | Bunnell et al. | 514/220 |
| 6,020,487 A | 2/2000 | Bunnell et al. | 540/557 |
| 6,348,458 B1 | 2/2002 | Hamied et al. | 514/220 |
| 2004/0048854 A1* | 3/2004 | Patel et al. | 514/220 |

FOREIGN PATENT DOCUMENTS

| CN | 1056693 | 12/1991 |
| EP | 0 454 436 A1 | 10/1991 |
| EP | 0 733 634 | 9/1996 |
| WO | WO 02/18390 | 3/2002 |
| WO | WO 02/060906 | 8/2002 |
| WO | WO 03/097650 | 11/2003 |
| WO | WO 2004/065390 A | 8/2004 |
| WO | WO 2004/094390 A | 11/2004 |

OTHER PUBLICATIONS

Calligaro, D.O., et al., "The synthesis and biological activity of some known and putative metabolites of the atypical antipsychotic agent olanzapine" *Bioorganic & Medicinal Chemistry Letters*, Oxford, GB, vol. 7, No. 1, Jan. 7, 1997, pp. 25-30.

* cited by examiner

*Primary Examiner*—Brenda L Coleman
(74) *Attorney, Agent, or Firm*—Kenyon & Kenyon LLP

(57) ABSTRACT

This invention encompasses methods of synthesizing olanzapine without solvents or by using low boiling organic solvents.

22 Claims, No Drawings

METHODS OF SYNTHESIZING OLANZAPINE

RELATED US APPLICATION DATA

This application claims the benefit of U.S. provisional application No. 60/532,126, filed Dec. 22, 2003; U.S. provisional application No. 60/547,901, filed Feb. 25, 2004; and U.S. provisional application No. 60/561,871, filed Apr. 12, 2004.

FIELD OF THE INVENTION

The invention encompasses methods of synthesizing olanzapine without solvents or by using low boiling organic solvents.

BACKGROUND OF THE INVENTION

Olanzapine is an antagonist of D-1 and D-2 dopamine receptors and also exhibits antimuscarinic and anticholinergic properties and antagonist activity at 5HT-2 receptor sites. Olanzapine also acts as an antagonist of noradrenergic alpha-receptors. These properties indicate that olanzapine may possess relaxant, anxiolytic, or anti-emetic properties and may be suitable for use as an a neuroleptic. Olanzapine is therefore useful in treating psychotic conditions including schizophrenia, schizophreni-form diseases, and acute mania. Olanzapine can additionally be used in the treatment of mild anxiety states when administered at lower doses.

Clinical evaluations of psychiatric patients suffering from schizophrenia have shown that olanzapine exhibits high levels of activity at surprisingly low dosage levels, making it a highly desirable therapeutic candidate for the treatment of psychotic patients. Unfortunately, olanzapine typically exhibits a color which is undesirable for commercial pharmaceutical use, especially as the color changes over time on exposure to air.

The current methods of synthesizing olanzapine require harsh reaction conditions, such as high temperatures and/or strong bases, such as alkyl lithium bases, with catalysts which may contribute to the undesirable color changes. To achieve the high reaction temperatures necessary in the current methods of synthesizing olanzapine, high boiling solvents that are difficult to remove once the product is obtained are used.

U.S. Pat. No. 5,229,382 discloses olanzapine synthesis by condensation of thienobenzodiazepine (4-amino-2-methyl-10H-thieno-[2,3-b][1,5]benzodiazepine) and N-methylpiperazine in a mixture of toluene and dimethylsulfoxide, which are high boiling organic solvents. The yield of the process is relatively low, and the solvent recovery is very difficult.

The invention encompasses methods of synthesizing olanzapine that do not require high boiling solvents or high temperatures.

SUMMARY OF THE INVENTION

One embodiment of the invention encompasses a method of synthesizing olanzapine under neat conditions, comprising heating a reaction mixture of N-methylpiperazine and thienobenzodiazepine (TBD) to about 110° C. to about 145° C.; maintaining the reaction mixture at about 110° C. to about 145° C. for at least 5 hours until olanzapine is synthesized; cooling the reaction mixture; adding water, at least two organic solvents, or water and at least one organic solvent, until olanzapine precipitates; and collecting the precipitated olanzapine. Optionally, the process may include further cooling steps.

The invention also encompasses methods of synthesizing olanzapine comprising combining TBD with N-methylpiperazine in a low boiling organic solvent to form a reaction mixture; heating the reaction mixture at reflux temperature for about 20 to about 24 hours; cooling the reaction mixture; adding water to the reaction mixture until olanzapine precipitates; and collecting olanzapine.

The methods of the invention may further comprise purging the reaction mixture during heating.

DETAILED DESCRIPTION OF THE INVENTION

The invention encompasses methods for synthesizing olanzapine using either no solvent or easily recoverable low boiling organic solvents and moderate reaction temperatures wherein solvent recovery is relatively simple. "Low boiling organic solvents" are pharmaceutically acceptable solvents with boiling points less than about 120° C., and preferably with boiling points less than about 100° C. Preferred low boiling organic solvents are those with boiling points between about 40° C. to about 120° C., and more preferably are those solvents with boiling points between about 50° C. to about 90° C. Preferred low boiling organic solvents include acetonitrile, which has a boiling point of about 81° C. to about 82° C. and is more environmentally friendly than the solvents used in the prior art. Another preferred low boiling organic solvent is acetone, which has a boiling point of about 56° C. It has been found that the lack of high boiling organic solvents increases the purity of crude olanzapine, simplifies the synthesis of olanzapine, and diminishes the potential for undesirable color changes upon exposing olanzapine to air.

During the synthesis of olanzapine, the reaction mixture may be purged with gas. Purging gas through the reaction mixture during heating mixes the reaction mixture and removes compounds which may become impurities in the final product, yielding olanzapine with fewer impurities, and thus, simplifying the purification process. For example, removing ammonia from the reaction mixture by purging yields olanzapine with fewer by-products, thereby simplifying the purification process.

Thienobenzodiazepine (TBD) used in the invention refers to 4-amino-2-methyl-10H-thieno-[2,3-b][1,5]benzodiazepine. TBD may be present as the hydrochloride acid salt or another stable acid salt. Preferably, TBD is present as thienobenzodiazepine hydrochloride. Thienobenzodiazepine may be present in the reaction mixture as the stoichiometrically limiting reagent. N-methylpiperazine is present in excess in the reaction mixture.

One embodiment of the invention encompasses a method of synthesizing olanzapine under neat conditions, comprising heating a reaction mixture of N-methylpiperazine and TBD to about 110° C. to about 145° C.; maintaining the reaction mixture at about 110° C. to about 145° C. for at least five hours until olanzapine is synthesized; cooling the reaction mixture; adding water, at least two organic solvents, or water and at least one organic solvent to precipitate olanzapine; and collecting the olanzapine.

TBD may be added after N-methylpiperazine is heated. Typically, the molar ratio of thienobenzodiazepine hydrochloride to N-methylpiperazine is about 1:3 to about 1:8, and preferably, the molar ratio is about 1:8. Preferably, the reaction mixture is heated under a nitrogen atmosphere. The reaction mixture is typically maintained at about 110° C. to about 145° C. for about 5 to about 6 hours, and preferably for about 5 hours. The mixture is preferably heated at about 125° C. Preferably, the reaction mixture is purged during heating by bubbling gas through the reaction mixture. Preferably, the gas is nitrogen gas and more preferably the gas is dry nitrogen gas.

The reaction mixture is preferably cooled to a temperature of less than about 100° C., more preferably to about room temperature to about 80° C., and most preferably to about 80° C.

Preferred organic solvents used to precipitate olanzapine include at least one of acetone, acetonitrile, tetrahydrofuran (THF), toluene and DMSO. When two organic solvents are used, the ratio of the two solvents is about 1:2 to about 1:10 by volume. The solvents may be added either concurrently or consecutively, e.g., at once or dropwise. One of ordinary skill in the art can easily determine the amount of solvents and water necessary to induce olanzapine precipitation with little or no experimentation.

Optionally, the process may include further cooling steps after adding water, at least two organic solvents, or water and at least one organic solvent, comprising graduated cooling of the reaction mixture to temperatures ranging from about 70° C. to about −5° C. Preferably, further cooling steps comprise cooling the reaction mixture to about 70° C. to below 10° C., more preferably to about 70° C. to about 0° C., even more preferably to about 70° C. to about 50° C., and most preferably to about 70° C. to about 60° C.

The reaction mixture may optionally be stirred overnight before collecting olanzapine. Olanzapine may be separated and collected from the reaction mixture using a variety of techniques known to the skilled artisan, e.g., by filtration or decantation.

Another embodiment of the invention encompasses methods of synthesizing olanzapine comprising combining TBD with N-methylpiperazine in a low boiling organic solvent to form a reaction mixture; heating the reaction mixture to about reflux temperature for about 20 to about 24 hours until olanzapine is synthesized; cooling the reaction mixture; adding water until olanzapine precipitates; and collecting olanzapine.

Typically, the molar ratio of TBD to N-methylpiperazine is about 1:3 to about 1:8. Preferred low boiling organic solvents which may be used in this method include, but are not limited to, acetone, acetonitrile, hexane, heptane and dimethylformamide. The reaction mixture may be purged during heating. Preferably, olanzapine is synthesized in about 22 hours. Preferably, the reaction mixture is cooled to about 22° C. to about 28° C.

Water is added to the reaction mixture in an amount sufficient to induce precipitation of olanzapine. One of ordinary skill in the art can easily determine the amount of water necessary to induce olanzapine precipitation with little or no experimentation. Factors that must be considered include the low boiling organic solvent used, the volume of low boiling organic solvent, the reaction amount, and other factors typically affecting the scale of the reaction. After the addition of water, the reaction mixture may be further cooled to about 10° C. to about −5° C. The precipitated olanzapine may be separated and collected from the reaction mixture using a variety of techniques known to the skilled artisan.

Having described the invention with reference to certain preferred embodiments, other embodiments will become apparent to one skilled in the art from consideration of the specification. The invention is further defined by reference to the following examples describing in detail the compositions, preparation of the compositions, and methods of administration of the invention. It will be apparent to those skilled in the art that many modifications, both to materials and methods, may be practiced without departing from the scope of the invention.

EXAMPLES

Example 1

Thienobenzodiazepine hydrochloride (TBD, 8.6 g, 32.3 mmol), N-methylpiperazine (30 ml, 27.1 g, 270 mmol), and acetone (30 ml) were added to a 100 ml round bottom flask equiped with a magnetic stirrer and a reflux condenser, forming a reaction mixture. The reaction mixture was heated to reflux (about 56° C.) under a nitrogen atmosphere. After 22 hours, the reaction mixture was cooled to about room temperature. Water (30 ml) was added to the reaction mixture, and the reaction mixture was cooled in an ice bath until olanzapine precipitated. Olanzapine (5.2 g) was collected by filtration in a yield of 51%, as determined by HPLC.

Example 2

Thienobenzodiazepine hydrochloride (TBD, 8 g, 30 mmol), N-methylpiperazine (15 ml, 13.5 g, 135 mmol), and acetonitrle (15 ml) were added to a 100 ml round bottom flask equiped with a magnetic stirrer and a reflux condenser and heated to reflux (about 81-82° C.) under a nitrogen atmosphere. After 22 hours, the reaction mixture was cooled to room temperature. Water (25 ml) was added to the reaction mixture. Upon a precipitate forming, additional water was added (25 ml) until the precipitate dissolved, and the mixture was stirred for 30 min. Olanzapine (5 g) was collected by filtration in a yield of 53%, as determined by HPLC.

Example 3

Thienobenzodiazepine hydrochloride (TBD, 8 g, 30 mmol), N-methylpiperazine (10 ml, 9.02 g, 90 mmol), and DMSO (15 ml) were added to a 100 ml round bottom flask equiped with a magnetic stirrer and a reflux condenser, forming a reaction mixture. The reaction mixture was heated to reflux (about 138° C.) under a nitrogen atmosphere. After 22 hours, the reaction mixture was cooled to room temperature. Water (30 ml) was added to the reaction mixture and the mixture was cooled in an ice bath until olanzapine precipitated. Olanzapine (5.1 g) was collected by filtration in a yield of 54%, as determined by HPLC.

Example 4

Thienobenzodiazepine hydrochloride (TBD, 8 g, 30 mmol), N-methylpiperazine (10 ml, 9.02 g, 90 mmol), and acetone (16 ml) were added to a 100 ml round bottom flask equiped with a magnetic stirrer and a reflux condenser, forming a reaction mixture. The reaction mixture was heated to reflux (about 56° C.) under a nitrogen atmosphere. After 24 hours, the reaction mixture was cooled to room temperature, and a solid formed. Water (50 ml) was added to the solid, which became granular. Olanzapine was collected by filtration in a yield of 91.6%, as determined by HPLC.

Example 5

In a 100 ml round bottom flask, N-methylpiperazine (9.75 ml, 8.8 g, 88 mmol) was heated in an oil bath to 125° C. under nitrogen for 10 min. Thereafter, thienobenzodiazepine hydrochloride (8 g, 30 mmol) was added to form a reaction mixture.

After 12 hours, the reaction mixture was cooled to room temperature. Water (12 ml) was added dropwise to the reaction mixture. Upon formation of a precipitate, additional water was added (12 ml) to the reaction mixture. The reaction mixture was stirred at room temperature. A granular solid formed and additional water (18 ml) was added. Olanzapine was collected by filtration in a yield of 84%, as determined by HPLC.

Example 6

In a 100 ml round bottom flask, N-methylpiperazine (11 ml, 10 g, 100 mmol) was heated in an oil bath to 125° C. under nitrogen for 10 min. Thereafter, thienobenzodiazepine hydrochloride (8 g, 30 mmol) was added to form a reaction mixture. After 12 hours, the reaction mixture was cooled to 80° C. Acetonitrile (20 ml) was added slowly to the reaction mixture via a funnel, whereupon a precipitate formed. Additional acetonitrile (30 ml) was added until the precipitate dissolved. The reaction mixture was removed from the oil bath and cooled to room temperature while stirring. After 10 min. a crystalline solid precipitated and after 90 min, the reaction mixture was cooled in an ice bath. The solid was collected by filtration, washed in acetonitrile, and determined to be olanzapine by HPLC (4.53 g, 93.3% yield).

Example 7

In a three necked flask, a reaction mixture of N-methylpiperazine (48 g, 480 mmol) and thienobenzadiazepine hydrochloride (16 g, 60 mmol) was heated in an oil bath to 125° C. while stirring and purging for 5 hours. Thereafter, the reaction mixture was allowed to cool to 80° C. and tetrahydrofuran (5 ml) and toluene (50 ml) were added separately. The reaction was stirred overnight, cooled in an ice bath for 1 hour, and a precipitate formed. The precipitate was collected by filtration and dried for 2 hours under vacuum, with pressure of less than 100 mm Hg, at 65° C. and determined to be olanzapine by HPLC (91.5% yield).

Example 8

In a three necked flask, a reaction mixture of N-methylpiperazine (30 g, 300 mmol) and thienobenzadiazepine hydrochloride (10 g, 37.6 mmol) was heated in an oil bath to 125° C. while stirring and purging for 5 hours. Thereafter, the reaction mixture was cooled to 80° C. Tetrahydrofuran (5 ml) was added to the reaction mixture, and toluene (32 ml) was added to the reaction mixture. The reaction was stirred overnight at room temperature (25° C. to 27° C.), cooled in an ice bath for 1 hour, and a precipitate formed. The precipitate was collected by filtration and washed (2×THF:toluene 5:32). The precipitate was then dried for 2 hours under vacuum at 65° C. and determined to be olanzapine by HPLC (88.8% yield).

Example 9

In a three necked flask, a reaction mixture of N-methylpiperazine (96 g, 960 mmol) and thienobenzadiazepine hydrochloride (32 g, 120 mmol) was heated in an oil bath to 125° C. while stirring and purging for 5 hours. Thereafter, the reaction mixture was allowed to cool to 80° C. and toluene (100 ml) was added followed by dropwise addition of water (50 ml). The reaction mixture was stirred overnight at room temperature, cooled in an ice bath for 1 hour, and a precipitate formed. The precipitate was collected by filtration and washed (2× toluene:water 2:1). The precipitate was then dried for 2 hours under vacuum at 65° C. and determined to be olanzapine by HPLC (91% yield).

Example 10

In a three necked flask, a reaction mixture of N-methylpiperazine (150 g, 1.5 mol) and thienobenzadiazepine hydrochloride (50 g, 0.188 mol) was heated in an oil bath to 145° C. while stirring and purging for 1.5 hours at a gentle reflux, and then for an additional 4.5 hours. The reaction mixture was monitored by HPLC until only 0.18% of thienobenzadiazepine remained. Thereafter, the reaction mixture was cooled to below 100° C. and toluene (200 ml), dimethylsulfoxide (200 ml) and water (200 ml) were added. The reaction mixture was cooled to 70° C. The reaction mixture was further cooled to 50° C., and a precipitate formed. The reaction mixture was stirred overnight at room temperature, cooled in an ice bath for 1 hour, and a precipitate formed. The precipitate was collected by filtration and washed (2× water, 40 ml). A wet solid was collected (66.2 g) and then dried overnight under vacuum at 65° C. to yield olanzapine (49.3 g, 85%).

The wet solid collected (5 g) was mixed in acetonitrile (36 ml) and water (22 ml) and heated to 80° C. until the material dissolved, forming a solution. The solution was cooled, and a precipitate formed. The solution was left to sit overnight. The solution was cooled in an ice bath, filtered, and the precipitate was collected by filtration. The precipitate was dried overnight under vacuum at 65° C., and determined to be olanzapine in 99.5% purity, by HPLC.

Example 11

Thienobenzodiazepine hydrochloride (50 g) and N-methylpiperazine (150 g) were added to a 1 liter reactor equipped with a mechanical stirrer, condenser, and thermometer, to form a reaction mixture. The reaction mixture was heated to 125° C. for five hours and cooled to 80° C. DMSO (200 ml) and toluene (200 ml) were added. The reaction mixture was cooled further to 60° C. and 200 ml of water was added. The reaction mixture was cooled further to 10° C. for 2 hours and heated to 50° C. for 2 hours. The reaction mixture was cooled to 10° C. and heated to 50° C. in the manner above two more times. The reaction mixture was cooled to 10° C. and stirred for 2 hours. A slurry resulted. The slurry was filtered under vacuum and washed with toluene (100 ml) and water (150 ml) and determined to be olanzapine (80.5 g, 99.5% purity) by HPLC.

What is claimed is:

1. A method of synthesizing olanzapine comprising:
   heating a reaction mixture of N-methylpiperazine and thienobenzodiazepine under neat conditions to about 110° C. to about 145° C.;
   maintaining the reaction mixture at about 110° C. to about 145° C. for at least 5 hours;
   cooling the reaction mixture;
   adding water, at least two organic solvents, or water and at least one organic solvent until olanzapine precipitates; and
   collecting the olanzapine.

2. The method of claim 1, wherein the reaction mixture is heated and maintained at about 110° C. to about 145° C. for about 5 to about 6 hours.

3. The method of claim 1, wherein the reaction mixture is heated and maintained at about 110° C. to about 145° C. for about 5 hours.

4. The method of claim 1, wherein heating a reaction mixture of N-methyl-piperazine and thienobenzodiazepine comprises heating N-methylpiperazine and adding thienobenzodiazepine to the heated N-methylpiperazine.

5. The method of claim 1, wherein the heating step is conducted under a nitrogen atmosphere.

6. The method of claim 1, wherein the reaction mixture is heated and maintained at about 125° C.

7. The method of claim 1, wherein the reaction mixture is cooled to a temperature of less than about 100° C.

8. The method of claim 1, wherein the reaction mixture is cooled to a temperature of about 80° C.

9. The method of claim 1, further comprising graduated cooling of the reaction mixture to a temperature of about 70° C. to about −5° C.

10. The method of claim 1, wherein the organic solvent is at least one of acetone, acetonitrile, tetrahydrofuran, toluene, or DMSO.

11. The method of claim 1, wherein at least two organic solvents are added.

12. The method of claim 11, wherein the ratio of the two solvents is about 1:2 to about 1:10 by volume.

13. The method of claim 1, wherein the molar ratio of thienobenzodiazepine to N-methylpiperazine is about 1:3 to about 1:8.

14. The method of claim 1, wherein the molar ratio of thienobenzodiazepine to N-methylpiperazine is about 1:8.

15. A method of synthesizing olauzapine comprising:
combining thienobenzodiazepine with N-methylpiperazine in a low boiling organic solvent to form a reaction mixture;
heating the reaction mixture to about reflux for about 20 to about 24 hours;
cooling the reaction mixture;
adding water to the reaction mixture; and
precipitating olanzapine.

16. The method of claim 15, wherein the low boiling organic solvent is at least one of acetone, acetonitrile, hexane, and heptane.

17. The method of claim 15, wherein the low boiling organic solvent is either acetone or acetonitrile.

18. The method of claim 15, wherein the molar ratio of thienobenzodiazepine to N-methylpiperazine is about 1:3 to about 1:8.

19. The method of claim 15, wherein the reaction mixture is cooled to room temperature.

20. The method of claim 15, further comprising cooling the reaction mixture to about 10° C. to about −5° C. after adding water.

21. The method of claims 1 or 15, further comprising purging the reaction mixture during heating.

22. The method of claim 21, wherein the purging is perfomed with nitrogen gas.

* * * * *

UNITED STATES PATENT AND TRADEMARK OFFICE
CERTIFICATE OF CORRECTION

PATENT NO. : 7,425,627 B2  
APPLICATION NO. : 11/020869  
DATED : September 16, 2008  
INVENTOR(S) : Dolitzky et al.

Page 1 of 1

It is certified that error appears in the above-identified patent and that said Letters Patent is hereby corrected as shown below:

Column 8, line 1, change "olauzapine" to -- olanzapine --

Signed and Sealed this

Twenty-second Day of September, 2009

David J. Kappos
*Director of the United States Patent and Trademark Office*